United States Patent
Joung et al.

(10) Patent No.: US 8,350,124 B2
(45) Date of Patent: Jan. 8, 2013

(54) **ROOT SPECIFIC EXPRESSION PROMOTER FROM *CAPSICUM ANNUUM* AQUAPORIN GENE AND USES THEREOF**

(75) Inventors: Young Hee Joung, Daejeon (KR); Do il Choi, Seoul (KR); Sang hyeob Lee, Daejeon (KR)

(73) Assignee: Young Hee Joung, Daejeon (KR)

( * ) Notice: Subject to any disclaimer, the term of this patent is extended or adjusted under 35 U.S.C. 154(b) by 127 days.

(21) Appl. No.: 12/735,818

(22) PCT Filed: Feb. 18, 2009

(86) PCT No.: PCT/KR2009/000758
§ 371 (c)(1),
(2), (4) Date: Aug. 19, 2010

(87) PCT Pub. No.: WO2009/104893
PCT Pub. Date: Aug. 27, 2009

(65) Prior Publication Data
US 2012/0090048 A1    Apr. 12, 2012

(30) Foreign Application Priority Data

Feb. 19, 2008 (KR) .................. 10-2008-0014764

(51) Int. Cl.
*C12N 15/82* (2006.01)
*C12N 15/10* (2006.01)
*C07H 21/04* (2006.01)
*A01H 5/00* (2006.01)

(52) U.S. Cl. ..... 800/287; 800/278; 800/295; 435/320.1; 536/24.1

(58) Field of Classification Search .................. None
See application file for complete search history.

*Primary Examiner* — Brent T Page
(74) *Attorney, Agent, or Firm* — The PL Law Group, PLLC

(57) ABSTRACT

The present invention relates to a root specific plant expression promoter and 5'-untranslated region (5'-UTR) from Aquaporin gene of *Capsicum annuum*, a root specific plant expression vector comprising the same, a process for root specif-expression of a foreign gene by using said vector, and a plant transformed with said vector and seeds of the transformed plant. According to the present invention, the root specific expression promoter of the present invention can be used for root specific expression of a gene that is introduced to a transformed plant, compared to CaMV35S promoter from cauliflower mosaic virus by which gene expression is promoted in entire tissues of a plant. Consequently, the claimed invention can be advantageously used for the development of a transformed plant which is desired to be used for production of a useful material in a plant root.

7 Claims, 4 Drawing Sheets

Fig. 1 [SEQ ID NO: 1]

GTCTTATATGAAAGGATGATCTCTTTTGTTATATTAGCACTAAATTAATGATATTCGATC
ATTTTAAAATTTATACTTTACTAATAATTTTTTGTAATTTTTAAATTACTAGATATTATA
TGTCAAACTAGGTAGTTGATAATTGACATGACTTAATTAAAGATAATGATGCAACGTTAT
CTTCAAATACTGAGTTCGCCTCTACGCATAGCTCAAAAAAATCTAAAAGAATTAAAGATT
TTGACAGTTCCACCATACTTGTATTTTTCTTATTTTTCAGGGTTGATTATTTTACTTTTT
TTTTTCTTAGTTTAGAATCTATCAAAAGAGGTCTTTTACCACACAAAAATAAAAGTAAA
ATTTGTATATATCCTATTCTCTCTCAGACCTCACGTACACAAGAGTAACAATTGTTGTTG
TTGTACAGGCCCACTACAAAAGTTGGTGATTAACCTGAGCAATAATTGTCATTTTTAAAG
CAAATTAATTATTTAATGACAGATTTAAAAAGAAGATTAAGAACCCTAGTTCCAGATGAT
TCCATGGTGCATGATTGCTCCGACCGAAAGCAATAACAAAGGGGTACTCCCATTCTTTCA
TGTCACTATCAAACAGAACCTACATGACGTGGCACTTTGTCTCCATTTACACGTGTCATC
AGCACAGCAATTTGGAGGTGAATTCTTAGCTGTCATTGCAGGCCTTTCGACCTCTACGGG
ACCGCTCGCCCACAATAAATTTGGTTTGAATCTTATATTACATGGTCCAAATTTTATTAT
ATTAACCGGTTACCTGCTATA

+1 *GCCGGTTCCTAACCCATCATGCCATTTACCAATTTCACAATATAAATCCATGCAAACTTT*
*CCCTACTTTCATCACTCTCTAGTTTATTTCCCCTCTTCAGTTTGGTTGTAGGCGAAATTT*
*TCTTCATTTTCAAATACCAATAACC* ATG

ROOT SPECIFIC EXPRESSION PROMOTER FROM CAPSICUM ANNUUM AQUAPORIN GENE AND USES THEREOF

CLAIM OF PRIORITY

This application makes reference to, incorporates the same herein, and claims all benefits accruing under 35 U.S.C. §119 from an application earlier filed in the Korean Intellectual Property Office on 19 Feb. 2008 and there duly assigned Ser. No. 10-2008-0014764. This application also makes reference to, incorporates the same herein, and claims all benefits accruing under 35 U.S.C. §365(c) of my PCT International application entitled ROOT SPECIFIC EXPRESSION PROMOTER FROM CAPSICUM ANNUUM AQUAPORIN GENE AND USES THEREOF filed on 18 Feb. 2009 and duly assigned Serial No. PCT/KR2009/000758.

TECHNICAL FIELD

The present invention relates to a root specific expression promoter from *Capsicum annuum* Aquaporin gene and uses thereof. More specifically, the present invention relates to a root specific expression promoter and 5'-untranslated region (5'-UTR) from *Capsicum annuum* Aquaporin gene, a root specific expression vector comprising the same, a plant transformed with said vector, a process for root specific expression of a foreign gene by using said vector, and a transformed plant which root-specifically expresses a foreign gene based on said process and seeds of the transformed plant.

BACKGROUND ART

Aquaporin is present inside a biomembrane of a plant and is a protein which is responsible for the transport of water. It is categorized into four separate groups including plasma membrane intrinsic protein (PIP), tonoplast intrinsic protein (TIP), nodulin 26-like intrinsic protein (NIP), and small and basic intrinsic protein (SIP) (Luu and Maurel, 2005, Plant Cell environ. 28: 85-96). Among these, expressions of some genes of the NIP group of *Arabidopsis thaliana* have been reported to be root specific and promoters for such genes have a root specific activity (Masahiro M, et. al., 2006, 47: 1420-1426).

Aquaporin gene from *Capsicum annuum* (a species of a hot pepper) is one kind of tonoplast intrinsic protein and there has no report until now indicating that a promoter from tonoplast intrinsic Aquaporin gene has a root specific activity.

Recently, various studies have been made to produce commercially useful materials based on a genetic engineering technology, i.e., with introduction of a foreign gene in a plant. When a commercially useful foreign gene is desired to be expressed in a transformed plant, a promoter that is related to expression of the gene is also required. For this, a promoter from cauliflower mosaic virus (CaMV35S), which is expressed in any type of a tissue of a plant, has been widely used. However, when it is desired to produce a useful material only in a root or when expression of a foreign gene in tissues other than a root has a harmful effect on a plant, a promoter which can induce expression specifically in a root is required.

In Korean Patent Reg. No. 0604186, a nucleotide sequence of a promoter for root specific expression of a sweet potato (*Ipomoea batatas* L.) storage roots, a vector for transient and root specific plant expression comprising the promoter sequence, and a method for transient expression in storage roots of a plant by using the expression vector are disclosed. In Korean Patent Reg. No. 0574563, a root specific expression promote from *Arabidopsis thaliana* and a vector comprising the promoter for root specific expression in plant are disclosed. However, these promoters are different from the promoter of the present invention.

DISCLOSURE OF INVENTION

Technical Problem

The present invention, which is devised in view of the necessities described in the above, is based on the finding that, when promoter and 5'-UTR of Aquaporin gene from *Capsicum annuum* is cloned, inserted to a binary vector, and then introduced to a model plant, *Arabidopsis thaliana*, a foreign gene is expressed specifically in a root tissue of *Arabidopsis thaliana*. Consequently, the present invention was completed.

Technical Solution

In order to solve the problems described in the above, the present invention provides a root specific plant expression promoter or 5'-UTR that are derived from Aquaporin gene of *Capsicum annuum*.

Further, the present invention provides a root specific plant expression promoter vector which comprises the above described root specific plant expression promoter and/or 5'-UTR, and a plant which is transformed with the expression vector.

Further, the present invention provides a process for root specific expression of a foreign gene by using the above described root specific expression promoter or 5'-UTR, when a useful substance is desired to be produced in large scale in a plant root.

Still further, the present invention provides a transformed plant prepared based on said process and seeds of the transformed plant, wherein said transformed plant root-specifically expresses a foreign gene.

Advantageous Effects

According to the present invention, with expression of a foreign gene in a plant using root specific expression promoter and/or 5'-UTR derived from Aquaporin gene from *Capsicum annuum* (hereinafter, abbreviated as CaAq), it was found that the promoter of the present invention is a novel promoter which can express a gene specifically in a plant root.

BRIEF DESCRIPTION OF DRAWINGS

FIG. 1 shows the nucleotide sequence [SEQ ID NO: 1] of the promoter and 5'-UTR of Aquaporin gene from *Capsicum annuum* (CaAq) of the present invention.

FIG. 3-B represents GUS enzymatic activity in transformed *Arabidopsis thaliana*.

MODE FOR THE INVENTION

Figure 2:
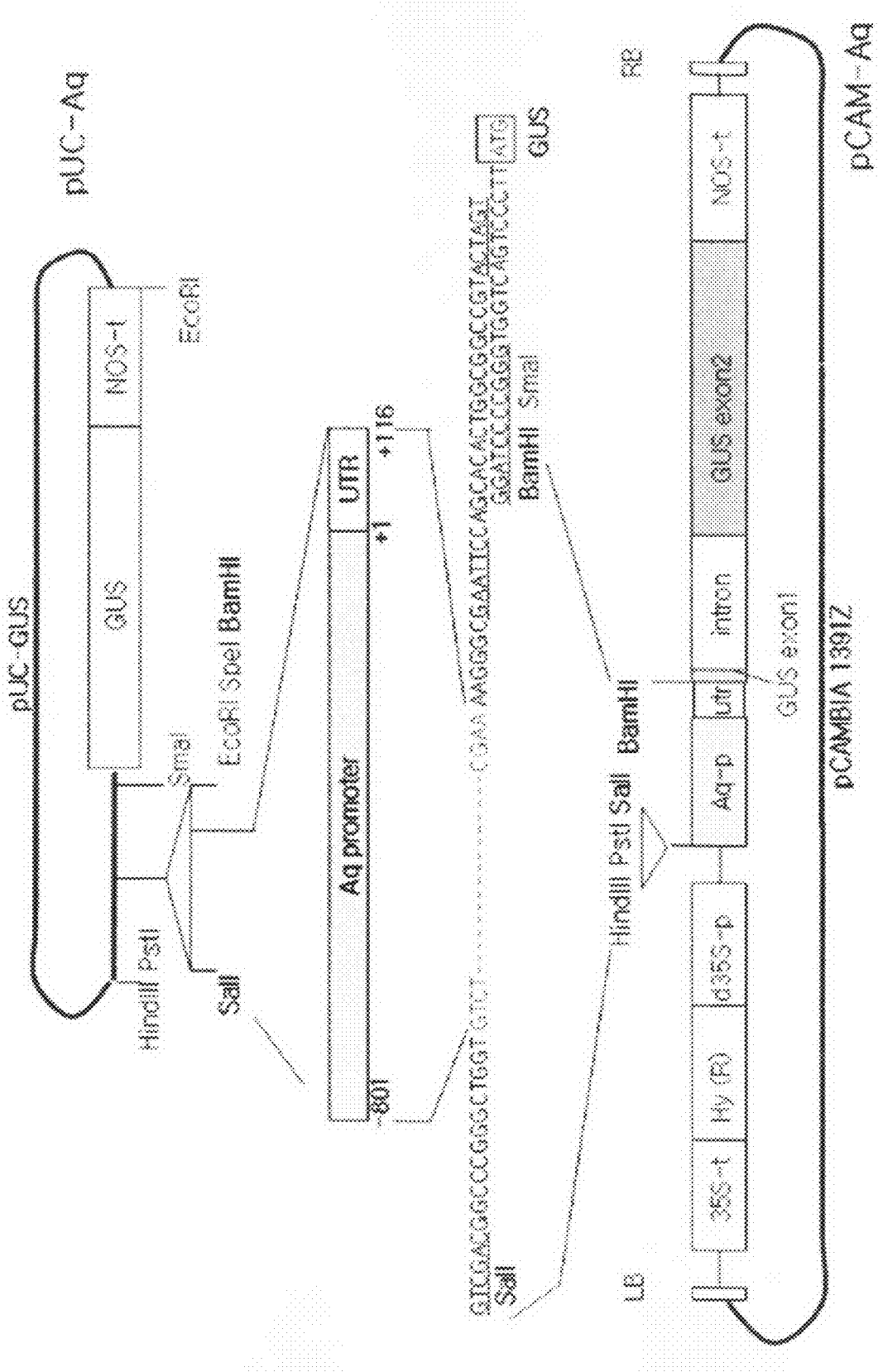
FIG. 2 is a schematic diagram showing plant expression vectors pCAM-Aq and pUC-Aq that are produced by inserting the promoter and part of 5'-UTR of CaAq gene to a reporter gene, β-glucuronidase (hereinafter, abbreviated as GUS).

In order to achieve the purpose of the invention as described in the above, the present invention provides a root specific plant expression promoter which comprises a nucleotide sequence of nucleotide base number 1 to number 801

(i.e., −801 to −1, starting from the transcription initiation site) of the sequence shown in FIG. 1 (SEQ ID NO: 1).

Compared to CaMV35S promoter from cauliflower mosaic virus by which gene expression is promoted in entire tissues of a plant, the root specific expression promoter of the present invention can be used for root specific expression of a gene that is introduced to a transformed plant.

In order to achieve the purpose of the invention as described in the above, the present invention also provides 5'-UTR comprising the nucleotide sequence of nucleotide base number 802 to number 946 (i.e., +1 to +145, starting from the transcription initiation site) of the sequence shown in FIG. 1 (SEQ ID NO: 1). Still further, according to one embodiment of the present invention, a plant expression vector in which part of 5'-UTR described above is comprised is constructed. Specifically, a plant expression vector comprising a nucleotide sequence from base number +1 to base number +116, numbered from the transcription initiation site of SEQ ID NO: 1, was constructed. Thus, the 5'-UTR of the present invention includes not only the nucleotide sequence from base number +1 to base number +116 numbered from the transcription initiation site of SEQ ID NO: 1 but also the nucleotide sequence from base number +1 to base number +145 numbered from the transcription initiation site of SEQ ID NO: 1.

In addition, a sequence variant of the above described promoter or 5'-UTR is also included in the scope of the present invention. The term "variant" means a nucleotide sequence which may have a different nucleotide sequence but has a similar functional characteristic compared to the nucleotide sequence of SEQ ID NO: 1. Specifically, the above described promoter sequence and 5'-UTR sequence may have a nucleotide sequence which has sequence homology of at least 70%, preferably at least 80%, more preferably at least 90%, still more preferably at least 95% compared to the nucleotide sequence of SEQ ID NO: 1.

Said "sequence homology %" for a certain polynucleotide is identified by comparing a comparative region with two sequences that are optimally aligned. In this regard, a part of the polynucleotide in comparative region may comprise an addition or a deletion (i.e., a gap) compared to a reference sequence (without any addition or deletion) relative to the optimized alignment of the two sequences.

In order to achieve another purpose of the present invention, the present invention provides a root specific plant expression vector which comprises a root specific plant expression promoter and/or 5'-UTR.

The root specific plant expression vector of the present invention may comprise only the promoter of the present invention, or 5'-UTR of the present invention can be used in combination with other general plant expression promoter such as CaMV 35S promoter. Preferably, however, having both the promoter and the 5'-UTR of the present invention is advantageous for obtaining root specific expression of a foreign gene introduced in a plant.

The root specific plant expression vector of the present invention may be used as a transient expression vector which can transiently express a foreign gene in a plant or as a plant expression vector which can permanently express a foreign gene in a plant.

A binary vector which can be used for the present invention can be any binary vector comprising RB (right border) and LB (left border) of T-DNA which can transform a plant when it is present with Ti plasmid of *A. tumefaciens*. Preferably, pBI101 (Cat 6018-1, Clontech, USA), pBIN19 (Genbank Deposit No. U09365), pBI121, pCAMBIA and the like, which are often used by a skilled person in the pertinent art, are used.

According to one embodiment of the present invention, a root specific plant expression vector can be pUC-Aq or pCAM-Aq depicted in FIG. 2, but not limited thereto. pUC-Aq vector in which GUS reporter gene as one example of a foreign gene is inserted in pUC18 vector and the promoter and 5'-UTR are placed in front of the gene (see, FIG. 2) can be used for plant transformation based on particle bombardment and also for transient expression. In addition, the promoter and 5'-UTR of the present invention are inserted into a binary vector (pCAMBIA 1391Z) for analyzing a promoter to give pCAM-Aq (FIG. 2), wherein GUS gene is comprised. Then, the vector is used for plant transformation using *Agrobacterium*. It would be obvious for a skilled person in the art that said GUS reporter gene can be replaced with other target foreign gene.

The term "vector" is used herein to refer DNA fragment(s) and nucleotide molecules that are delivered to a cell. Vector can be used for the replication of DNA and be independently reproduced in a host cell. The terms "delivery system" and "vector" are often interchangeably used. The term "expression vector" means a recombinant DNA molecule comprising a desired coding sequence and other appropriate nucleotide sequences that are essential for the expression of the operatively-linked coding sequence in a specific host organism. A promoter, an enhancer, a termination signal and a polyadenylation signal that can be used for an eukaryotic cell are all publicly well known.

A preferred example of plant expression vector is Ti-plasmid vector which can transfer a part of itself, i.e., so-called T-region, to a plant cell when the vector is present in an appropriate host such as *Agrobacterium tumefaciens*. Other types of Ti-plasmid vector (see, EP 0 116 718 B1) are currently used for transferring a hybrid gene to protoplasts that can produce a new plant by appropriately inserting a plant cell or hybrid DNA to a plant genome. Especially preferred form of Ti-plasmid vector is a so-called binary vector which has been disclosed in EP 0 120 516 B1 and U.S. Pat. No. 4,940,838. Other appropriate vectors that can be used for introducing the DNA of the present invention to a host plant can be selected from a double-stranded plant virus (e.g., CaMV), a single-stranded plant virus, and a viral vector which can be originated from Gemini virus, etc., for example a non-complete plant viral vector. Use of said vector can be especially advantageous when a plant host cannot be appropriately transformed.

Expression vector preferably comprises at least one selection marker. Said selection marker is a nucleotide sequence having a property which allows a selection based on a common chemical method. Any kind of gene that can be used for the differentiation of transformed cells from non-transformed cells can be a selection marker. Example includes, a gene resistant to herbicide such as glyphosate and phosphinotricin, and a gene resistant to antibiotics such as kanamycin, G418, bleomycin, hygromycin, and chloramphenicol, but not limited thereto.

With respect to a terminator for a plant expression vector of one embodiment of the present invention, any typical terminator can be used. Examples thereof include nopaline synthase (NOS), rice a-amylase RAmy1A terminator, phaseoline terminator, a terminator for octopine gene of *Agrobacterium tumefaciens* and the like, but not limited thereto.

In order to achieve another purpose of the present invention, the present invention provides *E. coli* or *Agrobacterium*

*tumefaciens* that is transformed with the root specific plant expression vector of the present invention.

In order to achieve another purpose of the present invention, the present invention provides a plant that is transformed with the root specific plant expression vector of the present invention and seeds of the plant.

The root specific plant expression vector of the present invention can be used for transformation of any plant including a dicot and a monocot plant. In the present invention, transformation was carried out using *Arabidopsis*. The plant according to one embodiment of the present invention can be a dicot plant such as potato, *Arabidopsis*, eggplant, tobacco, pepper, tomato, burdock, crown daisy, lettuce, Chinese bellflower, chard, spinach, sweet potato, celery, carrot, coriander, parsley, Chinese cabbage, cabbage, leaf mustard, watermelon, melon, cucumber, zucchini, gourd, strawberry, soy bean, mung bean, kidney bean, sweet pea and the like.

Transformation of a plant means any method which can transfer DNA to a plant. Such transformation is not necessarily required to have a period for regeneration and/or tissue culture. Transformation of a plant is now generally carried out not only for a dicot plant but also for a monocot plant. In principle, any method for transformation can be used for introducing a heterologous DNA of the present invention to a progenitor cell. Transformation can be carried out according to any method selected from a calcium/polyethylene glycol method for protoplasts (Krens, F.A. et al., 1982, Nature 296, 72-74; Negrutiu I. et al., June 1987, Plant Mol. Biol. 8, 363-373), an electroporation method for protoplasts (Shillito R. D. et al., 1985 Bio/Technol. 3, 1099-1102), a microscopic injection method for plant components (Crossway A. et al., 1986, Mol. Gen. Genet. 202, 179-185), a particle bombardment method for various plant components (DNA or RNA-coated) (Klein T. M. et al., 1987, Nature 327, 70), or a (non-complete) viral infection method in Agrobacterium tumefaciens mediated gene transfer by plant invasion or transformation of fully ripened pollen or microspore (EP 0 301 316), etc. According to the present method, *Agrobacterium* mediated DNA transfer is preferred. In particular, so-called binary vector technique as disclosed in EP A 120 516 and U.S. Pat. No. 4,940,838 can be preferably adopted for the present invention.

The plant cell that is used for the plant transformation according to the present invention can be any plant cell. The plant cell can be a cultured cell, a cultured tissue, a cultured organ, or a whole plant, preferably a cultured cell, a cultured tissue or a cultured organ, and more preferably any form of a cultured cell.

The plant tissue includes either differentiated or undifferentiated plant tissue, including root, stem, leaf, pollen, seed, cancerous tissue and cell lines having various shape that are used for culture, i.e., single cell, protoplast, bud and callus tissue, but not limited thereto. Plant tissue can be in planta or in a state of organ culture, tissue culture or cell culture.

In order to achieve another purpose of the invention, the present invention provides a process for root specific expression of a foreign gene in a plant comprising steps of:

carrying out recombination of a foreign gene in the root specific plant expression vector of the present invention, and transforming a plant with the recombinant plant expression vector.

Any gene which is desired to be expressed in a mass amount can be employed as a foreign gene. It is placed in the downstream region of the promoter and 5'-UTR in the root specific plant expression vector of the present invention, and if necessary, it can be expressed as being fused with a reporter gene. Transformation of a plant with the recombinant root specific expression vector of the present invention can be carried out according to the process as described in the above.

In order to achieve yet another purpose of the invention, the present invention provides a transformed plant that is produced according to the process described above wherein a foreign gene is root-specifically expressed, and seeds of the plant. The transformed plant can root-specifically express a foreign gene with an aid of a root specific expression promoter and 5'-UTR.

The present invention will now be described in greater detail with reference to the following examples. However, it is only to specifically exemplify the present invention and in no case the scope of the present invention is limited by these examples.

EXAMPLES

Example 1

Obtainment of a Promoter and 5'-UTR from CaAq Gene and their Sequencing

From the EST library of *Capsicum annuum*, nucleotide sequence of the Aquaporin gene and part of 5'-UTR were identified. To securely obtain the promoter and 5'-UTR for said gene, CaAq-specific primers were produced based on EST nucleotide sequence of KS01068H12 EST, i.e., AqGS1: GCA TGG TTA TTG GTA TTT GAA AAT GAA G (SEQ ID NO: 2) and AqGS2: TTC GCC TAC AAC CAA ACT GAA GAG GGG (SEQ ID NO: 3). Genomic DNA was extracted from young leaves of *Capsicum annuum*, and digested with restriction enzymes of Dra I, Eco RV, Pvu II, and Stu I based on a method provided by Universal Genome Walker Kit (Clontech). Then, after ligation with an adapter comprised in the kit, 4 different kinds of libraries were constructed. Based on these, first polymerase chain reaction (hereinafter, referred to as PCR) was carried out using GWAP1 adapter primer (GTA ATA CGA CTC ACT ATA GGG C (SEQ ID NO: 4)) and AqGS 1 primer, followed by dilution of 50 times. Then, by using GWAP2 adapter primer (ACT ATA GGG CAC GCG TGG T (SEQ ID NO: 5)) and AqGS22 primer, second PCR was carried out (see, FIG. 1). About 920bp DNA fragment which had been amplified by PCR was cloned in pCR-TOPO TA vector (Invitrogen, USA) and its nucleotide sequence was analyzed (FIG. 1). In the figure, italicized nucleotide sequence corresponds to 5'-untranslated region of the gene. In addition, initiation codon for protein synthesis, i.e., ATG, is written in bold letter and a site for transcription initiation is designated as "+1".

Example 2

Identification of Transcription Initiation Site for CaAq

In order to study the activity of the promoter site of CaAq, exact initiation site of gene transcription should be identified first. As such, based on cRACE (circular first-strand cDNA-mediated rapid amplification of cDNA ends; Nucleic Acid Research 23: 3796-3797, 1995), transcription initiation site for CaAq gene was determined first. Specifically, total RNA was isolated from young leaves of *Capsicum annuum*, and by using a reverse transcriptase (Super Script™ II RT, GIBCO BRL), a cDNA pool was established and then having it as a template and using a gene-specific primer ((CaAqRT1: 5'-AGC AAT TTG GCG GAT CGG CTA-3' (SEQ ID NO: 6) and CaAqRT2: 5'-GCA TGG TTA TTG GTA TTT GAA-3'

(SEQ ID NO: 7)) and an adapter primer of cDNA library ((RTAP1; 5'-CCA TCC TAA TAC GAC TCA CTA TAG GGC-3' (SEQ ID NO: 8) and RTAP2; 5'-ACT CAC TAT AGG GCT CGA GCG GC-3' (SEQ ID NO: 9)) PCR was carried out. As a result, it was confirmed that nucleotide base number 145 from the translation initiation codon (ATG) was identified as a transcription initiation site. In FIG. 1, it is marked with "+1" (FIG. 1).

Example 3

Construction of a Plant Expression Vector by using the Promoter and 5'-UTR of CaAq Gene The promoter and UTR fragment of CaAq gene, which had been obtained as shown in FIG. 1 and then inserted to pCR-TOPO TA vector, were digested with the restriction enzymes of SalI and BamHI. Resulting fragments were recovered and cloned in pUC18 vector (pUC-GUS) comprising GUS reporter gene to construct pUC-Aq. Also, with cloning in pCAMBIA 1391Z, pCAM-Aq vector was prepared and used for plant transformation using *Agrobacteria*.

Example 4

Transformation of *Arabidopsis thaliana* using the Plant Expression Vector of the Present Invention (pCAM-Aq)

*Agrobacterium tumefaciens* C58C1 was transformed with the plant expression vectors as prepared in the above, i.e., pCAM-Aq, pCAMBIA 1301, and pCAMBIA 1391Z, respectively, based on a freeze-thaw method (An, G. 1987, Methods in Enzymology, 153: 292-293). Each of the transformed *Agrobacteria* was cultured at 28° C. for two days under shaking. Then, using vacuum infiltration (Bechtold and Pelletier 1998, Methods Mol Biol 82:259-266), about five-week-old *Arabidopsis thaliana* (ecotype, Columbia) was transformed with them.

Example 5

Histochemical Staining and Enzymatic Analysis of Transformed *Arabidopsis thaliana*

Figure 3:
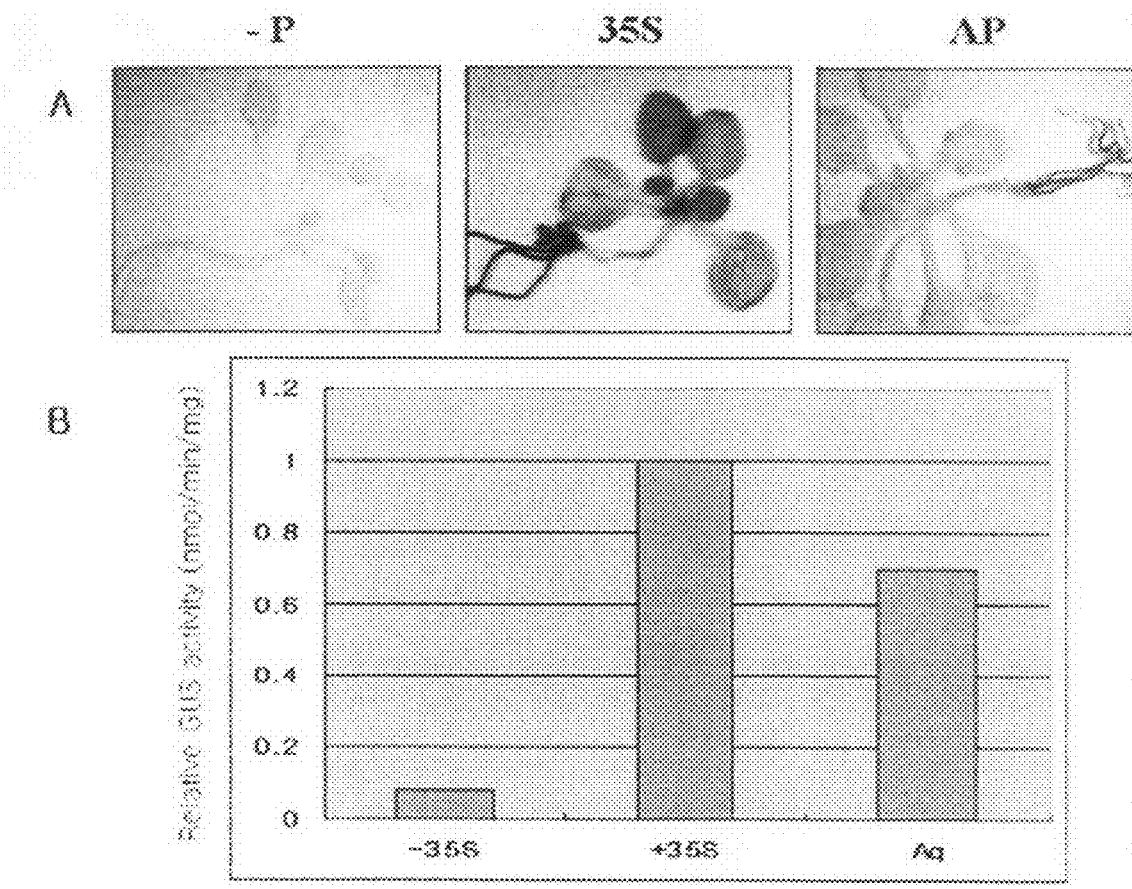
FIG. 3-A shows the results of GUS staining of *Arabidopsis thaliana* that have been transformed with pCAM-Aq (Aq), pCAMBIA1391Z (-P), or pCAMBIA 1301 (35S) that are shown in FIG. 2, respectively.

After harvesting seeds from the transformed *Arabidopsis thaliana* as produced in the above, they were added in MS culture medium comprising hygromycin (30 mg/L) and then a transformant having resistance to antibiotics was selected. From thus-selected transformed plants, GUS activity was determined based on a histochemical staining method and an enzymatic method. In order to stain whole tissue of each of the transformed plants, plant tissues were reacted in a solution comprising 1 mM X-glu (5-bromo-4-chloro-3-indolyl-β-glucuronide), 100 mM sodium phosphate (pH 7.0), 10 mM EDTA, 0.5 mM potassium ferricyanide, 0.5 mM potassium ferrocyanide and 0.1% Triton X-100 at 37° C. for 12 hours. Then, by using 100% ethanol, chlorophylls were removed. In FIG. 3-A, AP represents *Arabidopsis thaliana* transformed with pCAM-Aq, -P represents a control group wherein *Arabidopsis thaliana* was transformed with pCAMBIA 1391Z comprising GUS gene but no promoter, and 35S represents *Arabidopsis thaliana* which was transformed with pCAMBIA 1301 comprising GUS gene and CaMV35S promoter. As a result, it was found that, GUS activity is present in all the tissues transformed with pCAMBIA 1391Z comprising GUS gene, while in *Arabidopsis thaliana* that has been transformed with pCAM-Aq, GUS activity was found specifically in the root tissue.

Further, for quantitative analysis of GUS activity, each tissue of a transformed plant was ground in a solution comprising 50 mM sodium phosphate (pH 7.0), 10 mM EDTA, 0.1% Triton X-100, 0.1% sodium lauroylsarcosine and 10 mM β-mercaptoethanol, followed by centrifuge at 16,000 X g to obtain a supernatant, according to the method described by Jefferson et. al. (EMBO J. 6: 3901-3907, 1987). Thus obtained supernatant was admixed with 1 mM MUG (4-methylumbelliferyl glucuronide) and reacted at 37° C. The reaction was terminated by addition of 0.2 M $Na_2CO_3$. Fluorescence of the solution obtained after the termination of the reaction was measured by using a fluoromoter (excitation wavelength 360 nm and emission wavelength 460 nm). The measured value was then compared against a standard curve that is constructed by using MUG standard solution to obtain GUS activity. Results of the obtained GUS activity are shown in FIG. 3-B. The GUS activities shown in the figure are obtained from ten separate transformants ($T_1$ plant) that had been prepared for each construct. As a result, it was found that the promoter for CaAq gene of the present invention shows almost the same level of expression as CaMV35S promoter.

Figure 4:
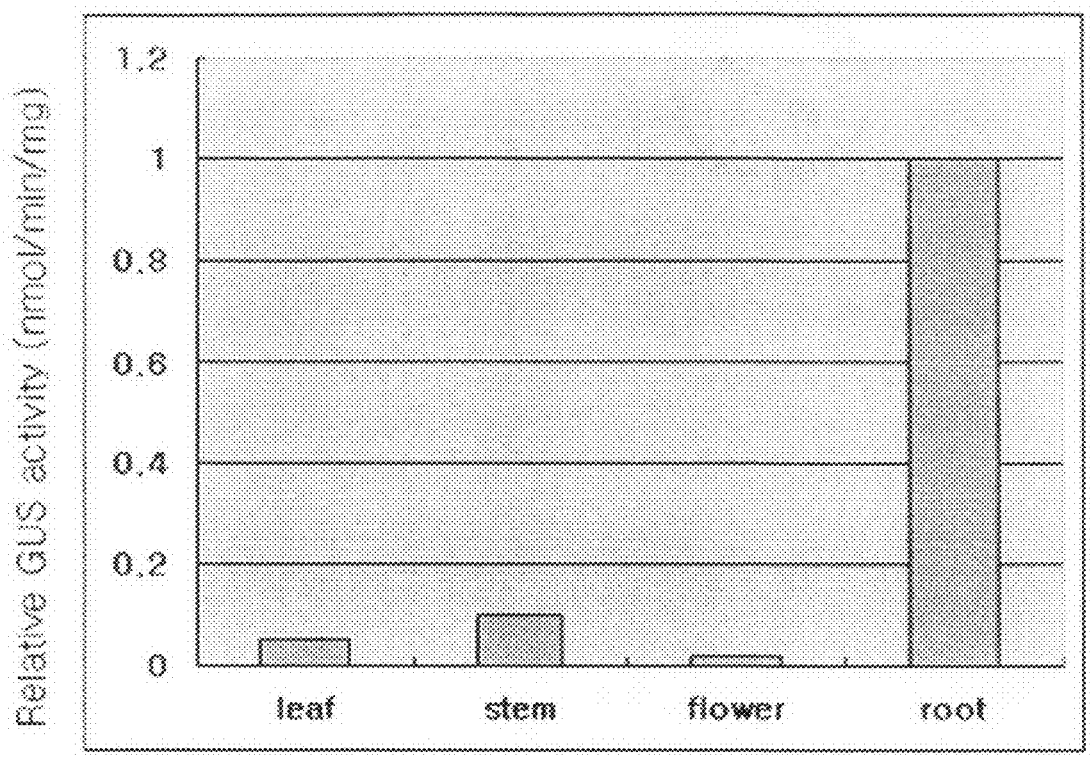
FIG. 4 shows the GUS enzymatic activity in different tissues of *Arabidopsis thaliana*.

Further, in a transformed *Arabidopsis thaliana*, GUS enzyme activity was determined for various tissues. As a result, it was found that in leaves, stems and flowers GUS was hardly expressed but it was expressed specifically in roots (FIG. 4). From this result, it was learned that expression of the promoter for CaAq gene is root specific.

The invention claimed is:

1. An isolated root specific plant expression promoter which comprises a nucleotide sequence of nucleotide base number 1 to number 801 (−801 to −1 region) of SEQ ID NO: 1.

2. An isolated 5'-UTR which comprises a nucleotide sequence of nucleotide base number 802 to number 946 (+1 to +145 region) of SEQ ID NO: 1.

3. A root specific plant expression vector comprising a root specific plant expression promoter which comprises a nucleotide sequence of nucleotide base number 1 to number 801 (−801 to −1 region) of SEQ ID NO: 1, 5'-UTR of claim 2, or the root specific plant expression promoter and the 5'-UTR.

4. The root specific plant expression vector according to claim 3, characterized in that it corresponds to pUC-Aq or pCAM-Aq depicted in FIG. 2.

5. *Agrobacterium tumefaciens* that is transformed with the root specific plant expression vector of claim 3.

6. A plant which is transformed with the root specific plant expression vector of claim 3.

7. A process for root specific expression of a foreign gene in a plant comprising steps of:
   carrying out recombination of a foreign gene in the root specific plant expression vector of claim 3, and transforming a plant with the recombinant plant expression vector.

* * * * *

SEQUENCE LISTING

```
<160> NUMBER OF SEQ ID NOS: 9

<210> SEQ ID NO 1
<211> LENGTH: 949
<212> TYPE: DNA
<213> ORGANISM: Capsicum annuum

<400> SEQUENCE: 1
gtcttatatg aaaggatgat ctcttttgtt atattagcac taaattaatg atattcgatc      60
attttaaaat ttatacttta ctaataattt tttgtaattt ttaaattact agatattata     120
tgtcaaacta ggtagttgat aattgacatg acttaattaa agataatgat gcaacgttat     180
cttcaaatac tgagttcgcc tctacgcata gctcaaaaaa atctaaaaga attaaagatt     240
```

```
ttgacagttc caccatactt gtattttcct tattttcag ggttgattat tttacttttt      300
tttttcttag tttagaatct atcaaaaaga ggtcttttac cacacaaaaa taaaagtaaa      360
atttgtatat atcctattct ctctcagacc tcacgtacac aagagtaaca attgttgttg      420
ttgtacaggc ccactacaaa agttggtgat taacctgagc aataattgtc attttttaaag     480 caaattaatt atttaatgac agatttaaaa agaagattaa gaaccctagt tccagatgat      540
tccatggtgc atgattgctc cgaccgaaag caataacaaa ggggtactcc cattctttca      600
tgtcactatc aaacagaacc tacatgacgt ggcactttgt ctccatttac acgtgtcatc      660
agcacagcaa tttggaggtg aattcttagc tgtcattgca ggcctttcga cctctacggg      720
accgctcgcc cacaataaat ttggtttgaa tcttatatta catggtccaa attttattat      780
attaaccggt tacctgctat agccggttcc taacccatca tgccatttac caatttcaca      840
atataaatcc atgcaaactt tccctacttt catcactctc tagtttattt ccctcttca       900 gtttggttgt aggcgaaatt ttcttcattt tcaaatacca ataaccatg                  949

<210> SEQ ID NO 2
<211> LENGTH: 28
<212> TYPE: DNA
<213> ORGANISM: Artificial Sequence
<220> FEATURE:
<223> OTHER INFORMATION: AqGS1 primer

<400> SEQUENCE: 2
gcatggttat tggtatttga aaatgaag                                         28

<210> SEQ ID NO 3
<211> LENGTH: 27
<212> TYPE: DNA
<213> ORGANISM: Artificial Sequence
<220> FEATURE:
<223> OTHER INFORMATION: AqGS2 primer

<400> SEQUENCE: 3
ttcgcctaca accaaactga agagggg                                          27

<210> SEQ ID NO 4
<211> LENGTH: 22
<212> TYPE: DNA
<213> ORGANISM: Artificial Sequence
<220> FEATURE:
<223> OTHER INFORMATION: GWAP1 adaptor primer

<400> SEQUENCE: 4
gtaatacgac tcactatagg gc                                               22

<210> SEQ ID NO 5
<211> LENGTH: 19
<212> TYPE: DNA
<213> ORGANISM: Artificial Sequence
<220> FEATURE:
<223> OTHER INFORMATION: GWAP2 adaptor primer

<400> SEQUENCE: 5
actatagggc acgcgtggt                                                   19

<210> SEQ ID NO 6
<211> LENGTH: 21
<212> TYPE: DNA
<213> ORGANISM: Artificial Sequence
<220> FEATURE:
<223> OTHER INFORMATION: CaAqRT1 primer
```

```
<400> SEQUENCE: 6
agcaatttgg cggatcggct a                                              21

<210> SEQ ID NO 7
<211> LENGTH: 21
<212> TYPE: DNA
<213> ORGANISM: Artificial Sequence
<220> FEATURE:
<223> OTHER INFORMATION: CaAqRT2 primer

<400> SEQUENCE: 7
gcatggttat tggtatttga a                                              21

<210> SEQ ID NO 8
<211> LENGTH: 27
<212> TYPE: DNA
<213> ORGANISM: Artificial Sequence
<220> FEATURE:
<223> OTHER INFORMATION: RTAP1 primer

<400> SEQUENCE: 8
ccatcctaat acgactcact atagggc                                        27

<210> SEQ ID NO 9
<211> LENGTH: 23
<212> TYPE: DNA
<213> ORGANISM: Artificial Sequence
<220> FEATURE:
<223> OTHER INFORMATION: RTAP2 primer

<400> SEQUENCE: 9
actcactata gggctcgagc ggc                                            23
```